(12) United States Patent
Clayman et al.

(10) Patent No.: US 6,773,432 B1
(45) Date of Patent: Aug. 10, 2004

(54) ELECTROSURGICAL SNARE

(75) Inventors: Ralph V. Clayman, Irvine, CA (US); William C. Collyer, St. Louis, MO (US); Jaime Landman, St. Louis, MO (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 10/110,159

(22) PCT Filed: Oct. 13, 2000

(86) PCT No.: PCT/US00/28675

§ 371 (c)(1),
(2), (4) Date: Apr. 5, 2002

(87) PCT Pub. No.: WO01/26571

PCT Pub. Date: Apr. 19, 2001

Related U.S. Application Data

(60) Provisional application No. 60/159,321, filed on Oct. 14, 1999.

(51) Int. Cl.$^7$ ................................................ A61B 17/39
(52) U.S. Cl. ........................... 606/41; 606/113; 606/45; 606/46; 606/47; 606/49
(58) Field of Search ............................. 606/45–49, 113

(56) References Cited

U.S. PATENT DOCUMENTS

| | | | |
|---|---|---|---|
| 4,171,700 A | 10/1979 | Farin ...................... | 128/303.14 |
| 4,311,143 A | 1/1982 | Komiya .................. | 128/303.15 |
| 4,318,409 A | 3/1982 | Oosten ................... | 128/303.14 |
| 4,559,943 A | 12/1985 | Bowers .................. | 128/303.14 |
| 4,676,243 A | 6/1987 | Clayman .................... | 128/303 |
| 4,788,977 A | 12/1988 | Farin et al. ............ | 128/303.13 |
| 4,860,745 A | 8/1989 | Farin et al. ............ | 128/303.17 |
| 4,969,885 A | 11/1990 | Farin ............................ | 606/38 |
| 5,078,716 A | 1/1992 | Doll ............................. | 606/47 |
| 5,158,561 A | 10/1992 | Rydell et al. ............... | 606/113 |
| 5,160,334 A | 11/1992 | Billings et al. ............... | 606/34 |
| 5,190,541 A | 3/1993 | Abele et al. .................. | 606/46 |
| 5,221,281 A | 6/1993 | Klicek .......................... | 606/45 |
| 5,324,288 A | 6/1994 | Billings et al. ............... | 606/45 |
| 5,366,476 A | 11/1994 | Noda .......................... | 606/206 |
| 5,370,645 A | 12/1994 | Klicek et al. ................. | 606/35 |
| 5,395,363 A | 3/1995 | Billings et al. ............... | 606/41 |
| 5,417,687 A | 5/1995 | Nardella et al. .............. | 606/32 |
| 5,423,809 A | 6/1995 | Klicek ......................... | 606/38 |
| 5,486,173 A | 1/1996 | Vancaillie .................... | 606/45 |
| 5,578,052 A | 11/1996 | Koros et al. ................. | 606/174 |
| 5,628,746 A | 5/1997 | Clayman ..................... | 606/45 |
| 5,766,167 A | 6/1998 | Eggers et al. ................. | 606/46 |
| 5,792,141 A | 8/1998 | Logeman ..................... | 606/46 |
| 5,800,482 A | * 9/1998 | Pomeranz et al. .......... | 607/101 |
| 5,855,061 A | 1/1999 | Malis et al. ................... | 29/825 |
| 5,893,847 A | * 4/1999 | Kordis ......................... | 606/41 |

(List continued on next page.)

*Primary Examiner*—Roy D. Gibson
*Assistant Examiner*—Aaron Roane
(74) *Attorney, Agent, or Firm*—Richard L. Myers

(57) ABSTRACT

An electrosurgical instrument includes a handle with a hollow elongate configuration and an electrosurgical assembly having ends disposed within the hollow handle and forming a continuous loop moveable by operation of the handle between an enlarged state and a contracted state. An electrosurgical element included in the assembly has an outer surface and axis and a lumen extending along the axis. Transverse portions of the element define a plurality of slots extending transverse to the axis and providing fluid communication between the lumen and the outer surface of the element. The element includes an insulated backbone and a plurality of ribs disposed to extend in space relationship to each other transverse to the backbone. A method of manufacture includes the step of creating slots in the element to define the ribs in the backbone.

19 Claims, 6 Drawing Sheets

U.S. PATENT DOCUMENTS

| | | | |
|---|---|---|---|
| 5,904,679 A | 5/1999 | Clayman | 606/39 |
| 5,925,040 A | 7/1999 | Nardella et al. | 606/41 |
| 5,931,836 A | 8/1999 | Hatta et al. | 606/38 |
| 6,007,546 A | 12/1999 | Snow et al. | 606/113 |
| 6,010,499 A | 1/2000 | Cobb | 606/40 |
| 6,039,734 A | 3/2000 | Goble | 606/41 |
| 6,056,746 A | 5/2000 | Goble et al. | 606/48 |
| 6,063,083 A | 5/2000 | Duong-Van | 606/45 |
| 6,346,106 B1 | 2/2002 | Jako | 606/47 |
| 6,402,746 B1 * | 6/2002 | Whayne et al. | 606/41 |

* cited by examiner

US 6,773,432 B1

ELECTROSURGICAL SNARE

CROSS REFERENCE TO RELATED APPLICATIONS

This is a Non-Provisional Application claiming the priority of Provisional Application Serial No. 60/159,321 filed on Oct. 14, 1999 and entitled Arching-Gap Electrosurgical Snare for Partial Nephrectomy, which is incorporated herein by reference.

BACKGROUND OF THE INVENTION

This invention relates generally to surgical instruments and more specifically electrosurgical instruments, as well as methods for performing a partial nephrectomy.

DISCUSSION OF THE PRIOR ART

A process for recovering the kidney of a patient is commonly referred to as a nephrectomy procedure. When only a portion of the kidney is to be removed, it is referred to as a partial nephrectomy. In this later instance, the procedure is primarily characterized by the nature of the organ itself which is highly vascularized. Cutting into the kidney therefore results in a large volume of blood loss. As a consequence, the partial nephrectomy procedure has been an open procedure which has provided immediate and general access to the organ.

This partial nephrectomy procedure is commonly performed using a scalpel to separate a diseased portion of the kidney from the remainder of the kidney. In order to control bleeding a separate instrument is used to cauterize the incision. The steps of cutting and cauterizing are performed repeatedly until the diseased portion is fully removed from the remainder of the kidney.

Snares are surgical instruments typically including a handle and a snare wire which forms a closed loop with the handle. As the wire is drawn into the handle, the size of the loop decreases and eventually severs any tissue within the loop. This procedure has most commonly been used for small appendages such as polyps that are typically nonvascular. Severing a polyp using a snare there does not create severe bleeding nor any reason to cauterize.

SUMMARY OF THE INVENTION

These disadvantages of the apparatus and procedures associated with the related art are overcome with the present invention which comprise an electrosurgical snare. The snare includes an electrosurgical element having a backbone and a plurality of ribs which are formed to control the electrosurgical current density. This element forms at least a portion of the snare loop and provides a capability for electrosurgical cutting as well as cauterizing.

In a method associated with the present invention, the electrosurgical snare is placed over a kidney in proximity T a diseased portion of the kidney. The electrosurgical element is moved into the kidney cutting the diseased portion from the remainder of the organ Importantly, cauterization occurs simultaneously with the cutting step so that the bleeding is immediately controlled in the procedure. The snare is provided with a low profile state to facilitate insertion through a trocar in a laparoscopic procedure.

In one aspect of the invention, an electrosurgical instrument includes a handle having an elongated configuration and extending between a proximal end and a distal end. An electrosurgical assembly extends from the distal end of the handle and forms a continuous loop. The assembly is moveable by operation of the handle between an enlarged state, wherein the continuous loop has a first size, and a contracted state, wherein the continuous loop has a second size smaller than the first size. An electrosurgical element is included in the assembly, the element having an outer surface, an axis, and a lumen extending along the axis. Transverse portions of the electrosurgical element define a plurality of slots extending transverse to the axis and providing fluid communication between the lumen of the electrosurgical element and the outer surface of tile electrosurgical element.

In another aspect, the invention includes an electrosurgical element having an axis and a backbone disposed to extend longitudinally along the axis. A plurality of ribs are included in the electrosurgical element and dispose to extend in a spaced relationship to each other and in a transverse relationship to the backbone. Insulation is disposed to extend along the backbone.

In a method associated with the present invention, the electrosurgical instrument is manufactured by providing a handle having a longitudinal channel. An electrosurgical assembly is provided having a first end and a second end defining a closed loop and moveable within the longitudinal channel of the handle to vary the size of the loop. Slots are created in the electrosurgical element to form a plurality of ribs facing inwardly of the loop and a backbone facing outwardly of the loop. Insulation is placed over at least a portion of the backbone.

DESCRIPTION OF PREFERRED EMBODIMENTS AND BEST MODE OF THE INVENTION

Figure 1:
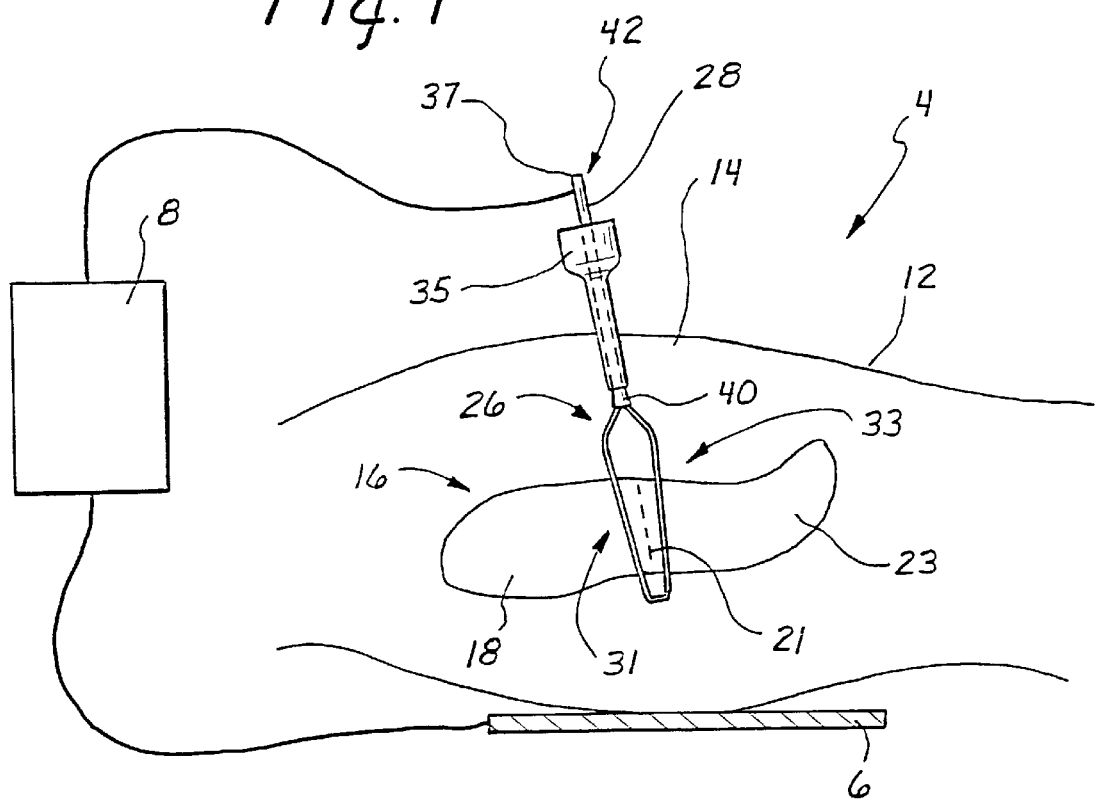
FIG. 1 is a side elevational view showing a laparoscopic partial nephrectomy procedure using an electrosurgical snare of the present invention.
Figure 4:
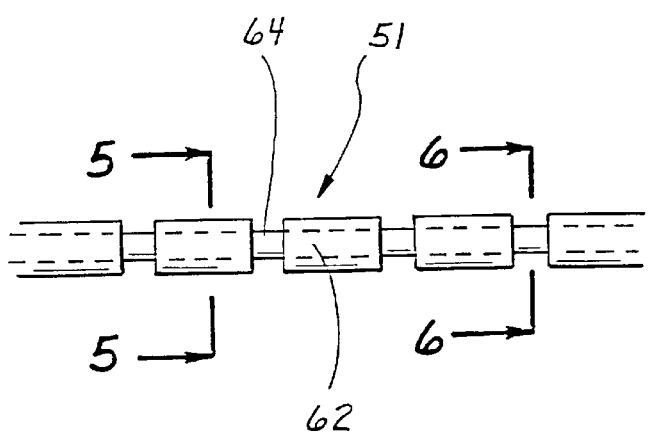
FIG. 4 is a side elevational view of an electrosurgical element associated with the electrosurgical snare.

In the side-elevational view of FIG. 1, a patient 4 is illustrated in a mono-polar electrosurgical procedure involving a ground plate 6 and an electrosurgical generator 8.

In the side-elevational view of FIG. 1, a patient 4 is illustrated with an abdominal wall 12 which defines an abdominal cavity 14 enclosing a kidney 16. In a partial nephrectomy procedure illustrated, a diseased portion 18 of the kidney 16 is to be severed along a dotted line 21.

In electrosurgical snare 26 of the present invention includes a handle 28 and an electrosurgical assembly 31 in the form of a loop on snare 33. The electrosurgical instrument 26 is sized and configured to fit through a trocar 35 which extends through the abdominal wall 12 in a laparoscopic procedure.

In the embodiment illustrated, the snare 33 is formed as a continuous loop with ends 35 and 37 which are directed through a distal end 40 of the handle 28 and operable from a proximal end 42 of the handle 28. In this embodiment the handle 28 functions as a sleeve and is moveable along the electrosurgical assembly 31 between a low profile insertion state, wherein the snare 33 has a relatively small size, and a high profile operative state wherein the snare 33 has a relatively large size. In the low profile state, the electrosurgical assembly can be easily inserted through the working channel of the trocar 35. When operatively disposed in the larger expanded state the snare 33 can be positioned around the kidney 16 as illustrated in FIG. 1. The electrosurgical assembly 31 can then be energized and moved toward its low profile state. This closes the snare 33 around the kidney 16 at the dotted line 21. As the electrosurgical assembly 31 cuts the kidney 16, it also cauterizes the cut area to inhibit bleeding which is commonly associated with these procedures. Once the diseased portion 18 is severed from the remainder 23 of the kidney 16, it can be removed through the trocar 35, or perhaps through a hand port (not shown).

Figure 2:
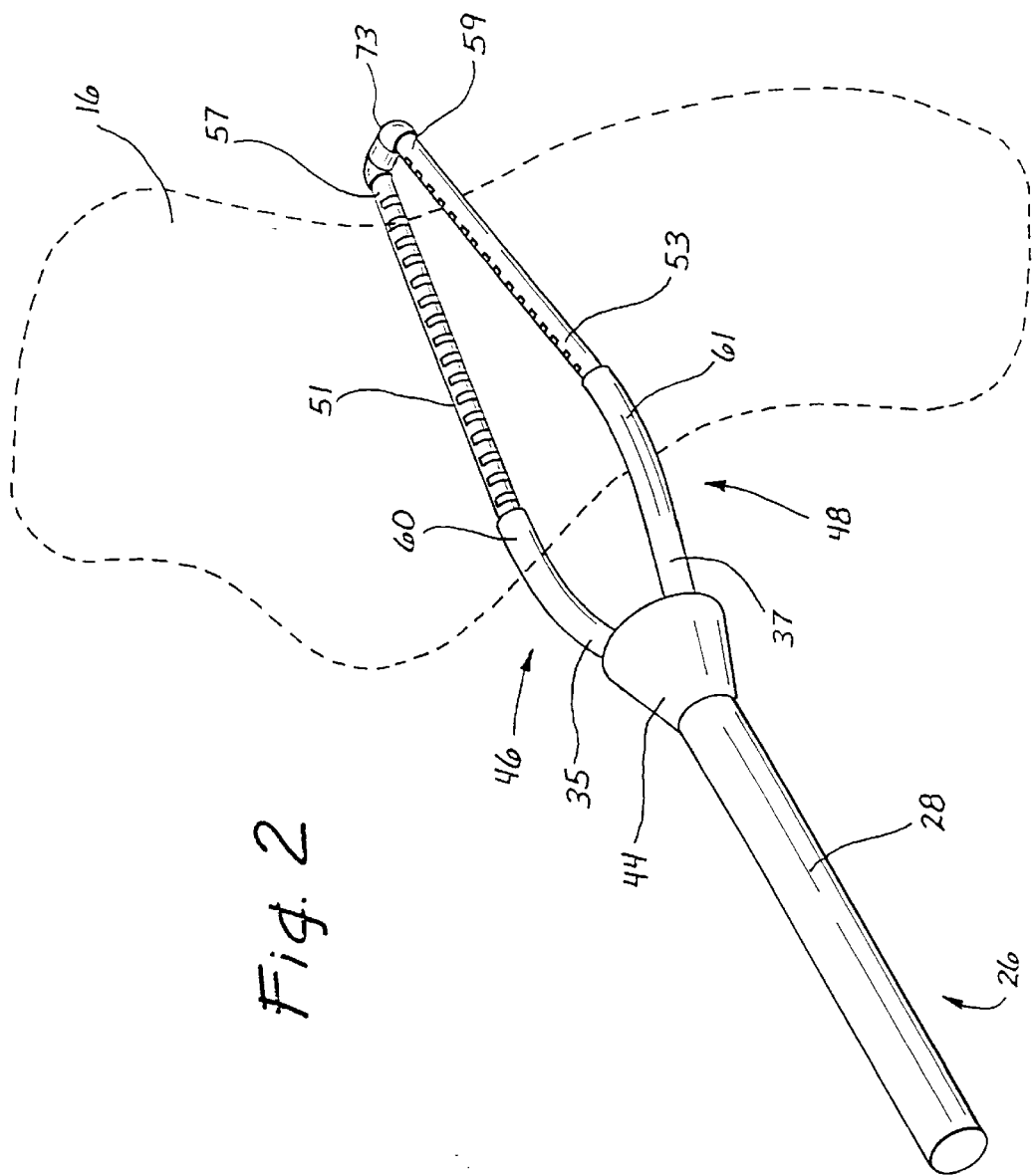
FIG. 2 is a perspective view of one embodiment of the electrosurgial snare of the present invention.

The perspective view of FIG. 2 shows the electrosurgical instrument 26 in greater detail. In this view it can be seen that the handle 28 preferably is formed as a hollow tube with a funnel 44 at its distal end. The electrosurgical assembly 31 is formed with a pair of opposing legs, 46 and 48, with their respective ends 36 and 37 extending through the funnel 44 into the handle 28.

In this embodiment, each of the legs 46 and 48 includes an electrosurgical element 51 and 53, respectively. The element can be formed from any electrically conductive material, but in the preferred embodiment, it is formed of hollow surgical stainless steel such as that used in hypodermic needles.

Figure 3:
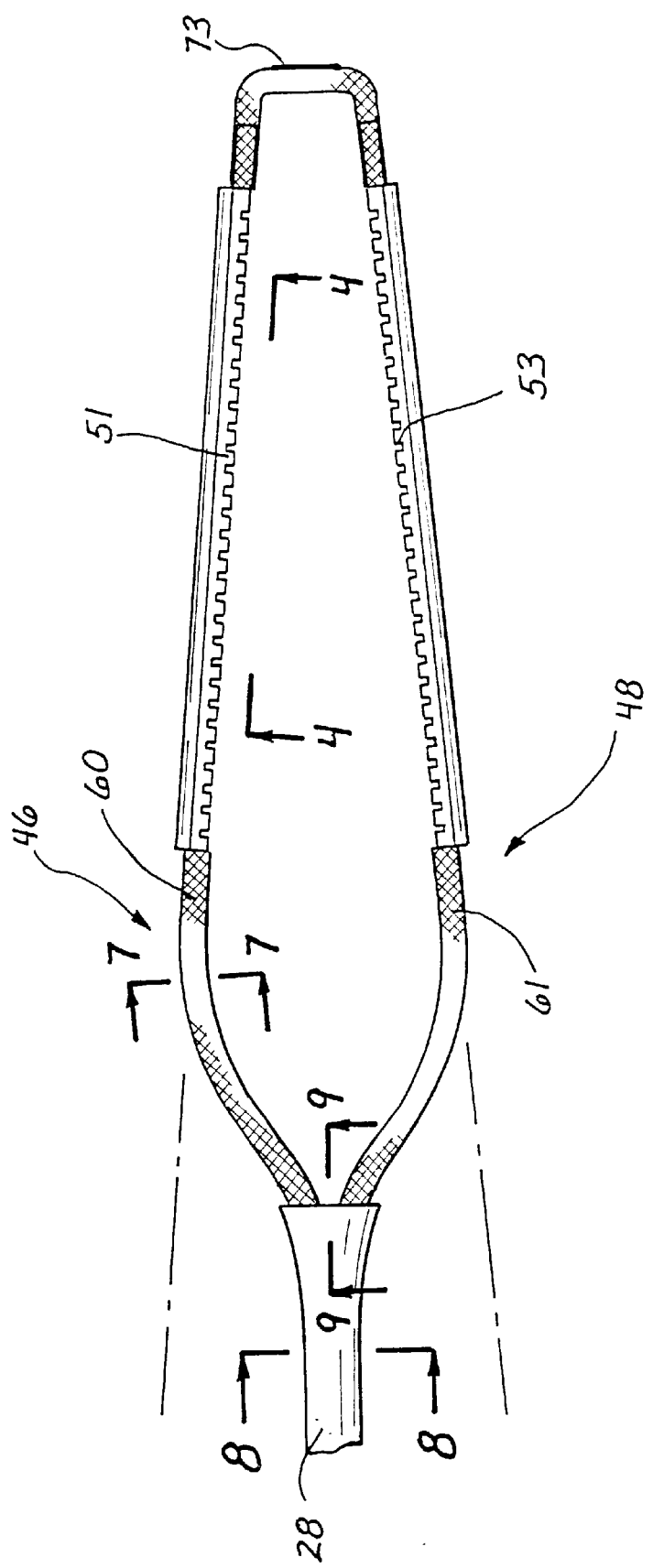
FIG. 3 is a top elevational view of the electrosurgical snare illustrated in FIG. 2.

As best illustrated in the top plan view of FIG. 3, the electrosurgical elements 51 and 53 can be similarly formed and disposed on opposite sides of the snare 33. With this relationship, the electrosurgical elements 51 and 53 have an inner side, which faces the opposite element, and an outer side, which faces away from the opposite element. For example, the electrosurgical element 51 can be provided with a generally straight configuration so that it extends along an axis 55 outwardly from the handle 28 to a distal end 57. Similarly, the electrosurgical element 53 extends to a distal end 59. In proximity to the funnel 44 the electrosurgical element 51 is covered by insulation tubing 60 to form a non-cutting portion of the element 51. The remaining portions of the element 51, which extend generally to the distal end 57, include a plurality of ribs 62 backbone, which extends generally along the axis 55, and a plurality of ribs 62 which extend inwardly of the backbone 64. The ribs 62 are separated by slots 66 which extend transversely, preferably perpendicular, to the axis 55. With this configuration, the ribs 62 face inwardly while the backbone 64 faces outwardly of the snare 33.

In operation, the electrosurgical elements 51 and 53 are energized by the generator 8 (FIG. 1), which causes cutting to occur where the rib 62 are in proximity to the tissue of the patent 4. In a particular embodiment, insulation covers 68 and 71 can be provided along the backbones of the respective electrosurgical elements 51 and 53 in order to inhibit cutting outwardly of the snare 33. At the distal ends 57 and 59 of the respective electrosurgical elements 51 and 53, an insulator 73 can be used to hold these ends in a generally closely-spaced, fixed, but slightly pivotal, relationship.

In operation, as the handle 28 and funnel 44 are advanced distally over the proximal end 36 and 37 of the electrosurgical elements 51 and 53. This causes the electrosurgical elements 51 and 53 to pivot at the insulator 73 in order to move the elements 51 and 53 against the tissue or kidney 16 captured by the snare 33. As the electrosurgical elements 51 and 3 move into close proximity with the tissue, the electrosurgical power emanating from the generator 8 cuts the tissue and simultaneously cauterized the cut area to inhibit bleeding.

Figure 5:
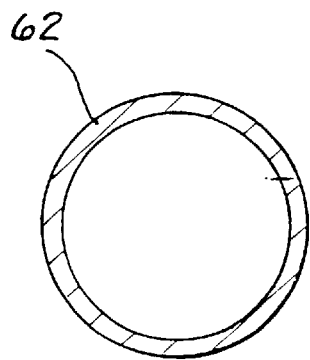
FIG. 5 is a cross-sectional view of the electrosurgical element taken alone lines 5—5 of FIG. 5.
Figure 6:
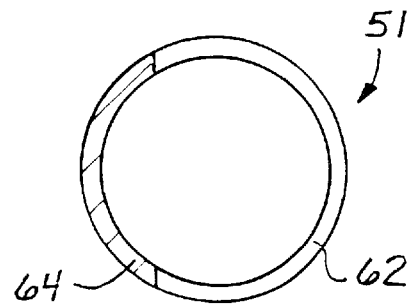
FIG. 6 is a cross-sectional view taken along lines 6—6 of FIG. 4.

In order to facilitate the cutting operation, the size and configuration of the slots 66, ribs 62 and backbone 64 can be carefully controlled. In a preferred embodiment, the electrosurgical element 51 is formed of surgical stainless steel and begins with a generally cylindrically configuration. Thus the element 51 initially has an inner diameter "d" and an outer diameter "D" as illustrated in FIG. 5. In order to form the slots 66, the cylindrical element 51 can be cut radially and generally perpendicular to the axis 55. A single one of the ribs 62 is formed between adjacent pairs of the slots 66. The depth of the cut forming the slots 66 will determine the size of the backbone with reference to FIG. 6, for example, it will be noted that a cut having a depth "P" which is greater than D/2, will provide the backbone 64 with a height "h" less than "D. This is off advantage in a preferred embodiment in order to ensure hat electrosurgical cutting does not occur at the backbone 64, but rather is restricted to the ribs 62.

In a preferred embodiment, the diameter D of the electrosurgical element 51 is 0.042 [in], the slots 62 are cut with a 1 [mm] width and spaced to provide the ribs 62 with a 1 [mm] width.

Figure 7:
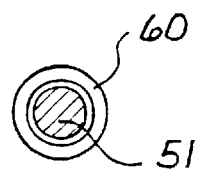
FIG. 7 is a cross-sectional view taken alone lines 7—7 of FIG. 3.
Figure 9:
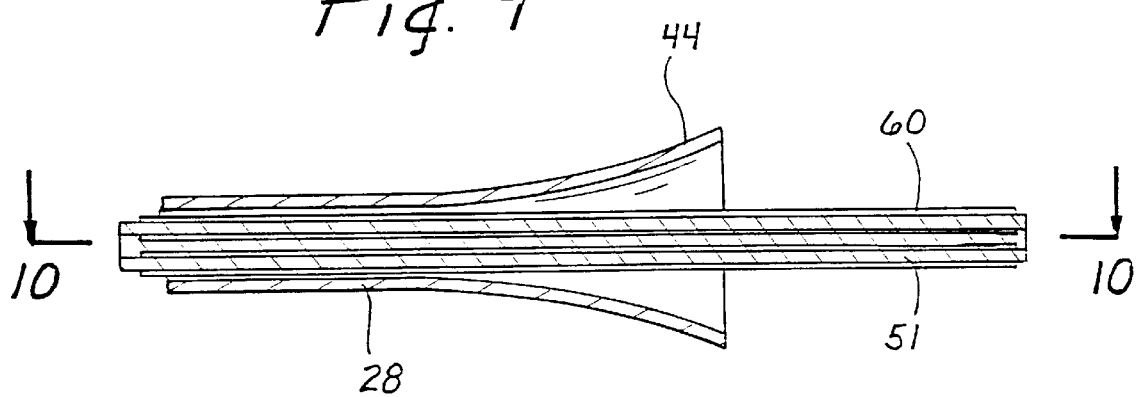
FIG. 9 is an axial cross-sectional view taken along lines 8—8 of FIG. 3.
Figure 10:
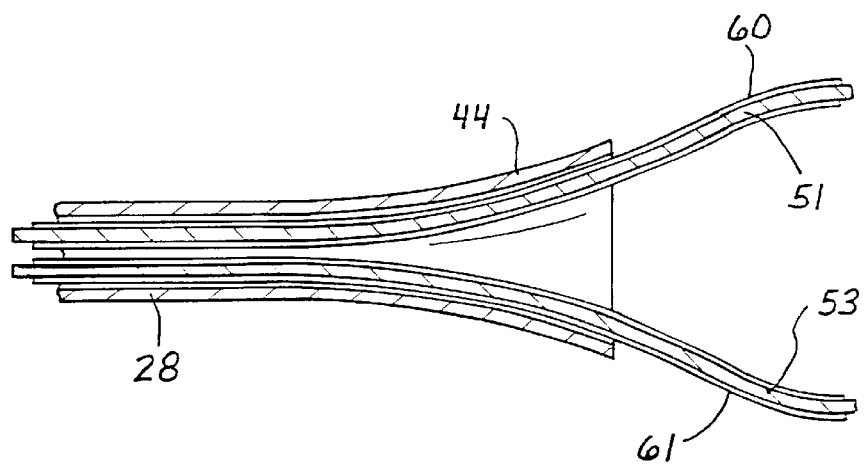
FIG. 10 is an axial cross-sectional view taken along lines 10—10 of FIG. 9.

The cross-sectional view of FIG. 7 shows the electrosurgical element 51 enclosed by the insulation cover 60 at the proximal end 35. The insulation cover 60 enables the two electrosurgical elements 51 and 53 to be moved into proximity with each other without establishing continuity. Thus the handle 28 and funnel 44 can be moved over the insulation tubes 60 and 61 to move the electrosurgical elements 51 and 53 toward each other and into proximity with the tissue to be cut.

Figure 8:
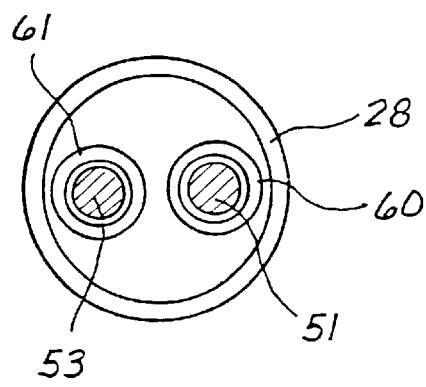
FIG. 8 is a cross-sectional view taken along lines 8—8 of FIG. 3.

The cross-sectional view of FIG. 8 shows two electrosurgical elements 51 and 53 covered by the respective insulation tubes 60 and 61 within the handle 28. It is the relative movement of the tube 28 and funnel 44 over the proximal insulated ends 35 and 37 of the elements 51 and 53, respectively, which closes the snare 33 against the tissue to be cut.

The cross-sectional view of FIG. 8 shows two electrosurgical elements 51 and 53 covered by the respective insulation tubes 60 and 61 within the handle 28. It is the relative movement of the tube 28 and funnel 44 over the proximal insulated ends 36 and 37 of the elements 51 and 53, respectively, which closes the snare 33 against the tissue to be cut.

Figure 11:
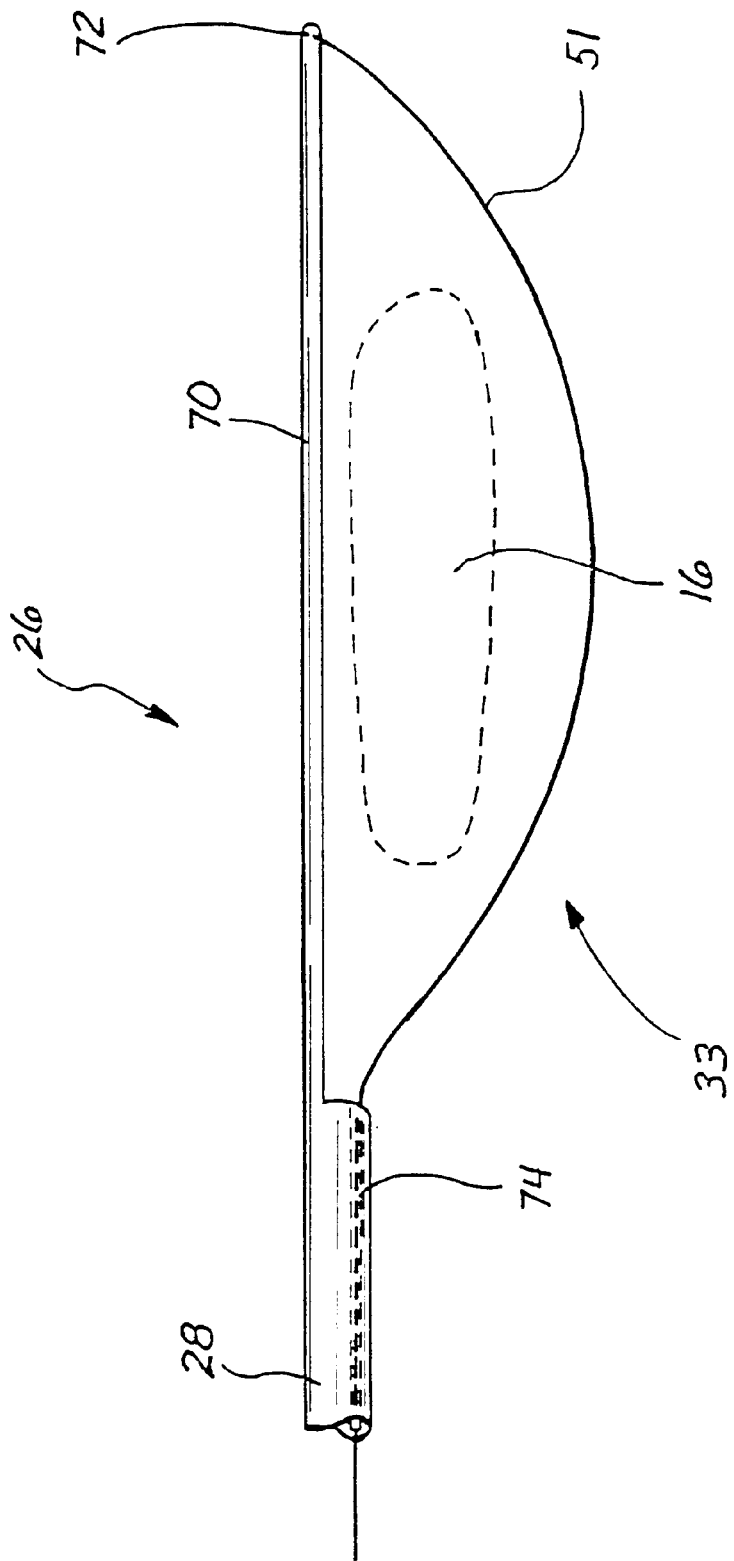
FIG. 11 is a top plan view of a further embodiment including a rigid extension arm and a single electrosurgical element.

A further embodiment of the invention is illustrated in FIG. 11 wherein the handle 28 includes a distal extension 75 which extends to a distal end 77. The electrosurgical element 51 is the only cutting element in this embodiment. Its distal end is attached to the distal end 77 of the extension 75 while its proximal end is moveably supported within a lumen 81 of the handle 28. In this embodiment, the snare 33 is defined by the extension 75 and the electrosurgical element 51.

The extension 75 is of particular advantage to this embodiment as it provides a generally rigid carrier for the distal end of the electrosurgial element 51. This facilitates not only insertion of the instrument 26 through the trocar 35 (FIG. 1), but also facilitates disposition of the snare 33 around the kidney 16. In this step of the process, the electrosurgical element 51 can be advanced through the lumen 81 in the handle 28 to form a loop and thereby enlarge the size of the snare 33. Using the generally rigid extension 75, the electrosurgical element 51 can then be more easily moved over the kidney 16 to its operative position.

Once the instrument 26 is operatively positioned over the kidney 16, the electrosurgical element 51 can be energized and drawn proximally through the lumen 81 relative to the handle 28. This will begin moving the element 51 into a more parallel relationship with the extension 70, closing the snare 33 around the kidney 16 and creating the desired cut through the kidney 16. As previously noted, the electrosurgical frequencies, provided by the generator 8 (FIG. 1) will not only cut the tissue, but simultaneously cauterize the tissue to inhibit bleeding. In this embodiment, cutting is restricted to only one side of the snare 33 and therefore is easier to control. The electrosurgical element 51 can be formed as in the previous embodiment where the slots 66, ribs 62, and backbone 64 can be controlled to provide the desired current density.

What is claimed is:

1. An electrosurgical instrument adapted for use with an electrosurgical generator to sever an element of tissue from a patient at an operative site, comprising:
    a handle having an elongate configuration and extending between a proximal end and a distal end;
    an electrosurgical assembly extending from the distal end of the handle and forming a continuous loop disposed generally in a loop plane, the electrosurgical assembly being free of any obstruction on at least one side of the loop plane to facilitate placement of the continuous loop over the element of tissue to be severed;
    the electrosurgical assembly being moveable by operation of the handle between an enlarged state wherein the continuous loop has a first size facilitating engagement of the element of tissue and a contracted state wherein the continuous loop has a second size smaller than the first size facilitating severance of the element of tissue from the patient;
    an electrosurgical element bent back on itself to form the continuous loop in the assembly, the electrosurgical element having an outer surface, an axis, and a lumen extending along the axis;
    portions of the electrosurgical element defining a plurality of slots providing fluid communication between the lumen and the outer surface to facilitate passage of a fluid between the lumen of the electrosurgical element and the operative site.

2. The electrosurgical instrument recited in claim 1, wherein;
    the electrosurgical element has the configuration of a cylinder with a radius; and
    the slots extend into the electrosurgical element a particular distance not less than the radius of cylinder.

3. The electrosurgical instrument recited in claim 1, further comprising:
    longitudinal portions of the electrosurgical element defining a backbone extending along the axis of the electrosurgical element and facing outwardly of the loop; and
    insulation disposed on the outer surface of the electrosurgical element along the backbone.

4. The electrosurgical instrument recited in claim 1, wherein each of the slots is disposed generally in a slot plane transverse to the axis of the electrosurgical element.

5. The electrosurgical instrument recited in claim 1, further comprising:
    a rigid arm included in the electrosurgical assembly and extending from the distal end of the handle to engage the electrosurgical element at a location spaced from the distal end of the handle.

6. The electrosurgical instrument recited in claim 5, further comprising:
    longitudinal portions of the electrosurgical element defining a backbone facing away from the arm of the electrosurgical assembly.

7. The electrosurgical instrument recited in claim 1, wherein the handle includes a hollow sleeve and the electrosurgical assembly is sized and configured to be moved into the sleeve toward the contracted state and to be moved out of the sleeve toward the enlarged state.

8. The electrosurgical instrument recited in claim 1, wherein the electrosurgical element is accessible at the proximal end of the handle to permit the injection of a fluid into the lumen, and through the lumen and the slots to the outer surface of the electrosurgical element.

9. The electrosurgical instrument recited in claim 1, wherein at least one of the slots has a first side defined in a first plane and a second side defined in a second plane generally parallel to the first plane.

10. The electrosurgical instrument recited in claim 1, wherein the electrosurgical element is a first electrosurgical element and the instrument further comprises a second electrosurgical element opposing the first electrosurgical element.

11. The electrosurgical instrument recited in claim 10, wherein the second electrosurgical element is coupled to the first electrosurgical element by an insulator.

12. An electrosurgical instrument adapted for use with an electrosurgical generator to sever tissue from a patient, comprising:
    a handle having an elongate configuration and extending between a proximal end and a distal end;
    an electrosurgical assembly extending from the distal end of the handle and being moveable by operation of the handle between an enlarged state and a contracted state;
    an electrosurgical element included in the electrosurgical assembly and having an axis, the element being bent back on itself to form a loop;
    a backbone disposed to extend longitudinal along the axis, the backbone facing generally outwardly of the loop;
    a plurality of ribs included in the electrosurgical element and disposed to extend in a spaced relationship to each other transverse to the backbone, the ribs facing generally inwardly of the loop; and
    insulation disposed along the backbone but not along the ribs to inhibit the cutting of tissue along the backbone and to facilitate the cutting of tissue along the ribs.

13. The electrosurgical instrument recited in claim 12 wherein the electrosurgical element in cross-section has the general shape of a circle.

14. The electrosurgical instrument recited in claim 13 wherein the electrosurgical instrument is hollow.

15. (Original) The electrosurgical element recited in claim 12 wherein at least two of the ribs are generally parallel to each other and generally perpendicular to the backbone.

16. A method of manufacturing an electrosurgical instrument adapted to produce an electrosurgical effect on body tissue, comprising the steps of:

providing a handle having a longitudinal channel;

providing an electrosurgical assembly having a first end and a second end defining a generally closed loop, at least one of the first end and the second end being moveable within the longitudinal channel of the handle to vary the size of the loop;

creating slots in the electrosurgical element to define a plurality of ribs facing inwardly of the loop, and a backbone facing outwardly of the loop;

placing insulation over at least a portion of the backbone to inhibit the electrosurgical effect outwardly of the loop; and during the placing step, ensuring that the insulation does not extend over at least a portion of the ribs to facilitate the electrosurgical effect inwardly of the loop.

17. The method recited in claim 16, further comprising the step of:

moving the electrosurgical assembly within the channel to enlarge the loop in order to facilitate placement of the loop around the body tissue.

18. The method recited in claim 17, further comprising the step of:

drawing the electrosurgical assembly into the channel to reduce the size of the loop around the body tissue and to facilitate the electrosurgical effect on the body tissue.

19. The method recited in claim 16 further comprising the step of:

passing a liquid through the slots to facilitate the electrosurgical effect between the electrosurgical element and the body tissue.

* * * * *